(12) United States Patent
Bowlsbey et al.

(10) Patent No.: US 9,463,075 B2
(45) Date of Patent: Oct. 11, 2016

(54) REPLACEABLE LIGHT SOURCE AND RADIATION GENERATING DEVICE INCLUDING THE SAME

(71) Applicant: SOUTHERN LINAC, LLC, Mandeville, LA (US)

(72) Inventors: Clark Bowlsbey, Mandeville, LA (US); Edward Q. Castle, Jr., Covington, LA (US); Kyle Bowlsbey, Covington, LA (US)

(73) Assignee: SOUTHERN LINAC, LLC, Mandeville, LA (US)

( * ) Notice: Subject to any disclaimer, the term of this patent is extended or adjusted under 35 U.S.C. 154(b) by 0 days.

(21) Appl. No.: 14/269,662

(22) Filed: May 5, 2014

(65) Prior Publication Data

US 2014/0239199 A1  Aug. 28, 2014

Related U.S. Application Data (63) Continuation-in-part of application No. 13/622,608, filed on Sep. 19, 2012, now Pat. No. 8,729,506.

(51) Int. Cl.
*F21V 19/00* (2006.01)

(52) U.S. Cl.
CPC .......... *A61B 90/30* (2016.02); *A61B 2090/309* (2016.02)

(58) Field of Classification Search
CPC .... A61B 19/52; A61B 19/5202; A61B 6/08; G21K 5/00
See application file for complete search history.

(56) References Cited

U.S. PATENT DOCUMENTS

| | | | |
|---|---|---|---|
| 3,861,807 A | | 1/1975 | Lescrenier |
| 5,654,996 A | | 8/1997 | Steinberg et al. |
| 8,077,830 B2 | | 12/2011 | Brown et al. |
| 2006/0139907 A1 | * | 6/2006 | Yen .................. H05B 33/0842 362/85 |
| 2008/0316736 A1 | * | 12/2008 | Hunnewell ............ A45C 15/06 362/187 |
| 2010/0165600 A1 | * | 7/2010 | Ku .......................... F21K 9/00 362/84 |
| 2010/0259190 A1 | * | 10/2010 | Aikala .................. A01G 7/045 315/294 |
| 2011/0037840 A1 | * | 2/2011 | Hiltl .................... A61B 19/5202 348/61 |

FOREIGN PATENT DOCUMENTS

| | | |
|---|---|---|
| EP | 2085117 B1 | 8/2012 |
| WO | WO-2014033425 A2 | 3/2014 |

OTHER PUBLICATIONS

Imaging & Oncology for imaging and therapy professionals 2013, Oncology Systems Limited, <http://www.radpro.eu/radproexpo2012/elekta/agility_white_paper_high_res.pdf>, Jul. 2014.

Frank Lohr, M.D., et al., Universitätsmedizin Mannheim, Medizinische Fakultät Mannheim der Universität Heidelberg, Prime Esperienze con Versa HD—Velocitá, Versatilitá e Precisione, <http://www.congressiairo.it/2013/Taormina2013/files/01_F.Lohr.pdf>, Jul. 2014.

Kevin Brown, Giulia Thompson; Elekta, Ltd., Agility Intelligent Design; <http://www.radpro.eu/radproexpo2012/elekta/agility_white_paper_high_res.pdf>; Jul. 2014.

510(k) Summary, Elekta Limited, Apr. 27, 2012.

Agility, Elekta's Innovative Beam-Shaping Solution for Cancer Treatment, Ships Globally; Elekta, Oct. 22, 2012.

Elekta to Demonstrate Agility Beam-shaping Solution at 2012 ASTRO Annual Meeting, dated Oct. 24, 2012, accessed Jul. 15, 2014.

Elekta's Agility Radiation Therapy Beam-shaping Innovation for Cancer Treatments Receives U.S. 510(k) Clearance, dated Jun. 22, 2012. accessed Jul. 15, 2014.

\* cited by examiner

*Primary Examiner* — Evan Dzierzynski (74) *Attorney, Agent, or Firm* — Marshall, Gerstein & Borun LLP (57) ABSTRACT

A replacement light apparatus includes a base plate a bearing member, and a light source. The bearing member extends from a portion of the base plate. The bearing member includes a bearing surface. The light source is coupled to the bearing surface of the bearing member and adapted to project a cone of light centered on an illumination axis that extends perpendicular to the bearing surface.

30 Claims, 7 Drawing Sheets

REPLACEABLE LIGHT SOURCE AND RADIATION GENERATING DEVICE INCLUDING THE SAME

CROSS-REFERENCE TO RELATED APPLICATIONS

The present application is a continuation-in-part of U.S. patent application Ser. No. 13/622,608, filed Sep. 19, 2012, the disclosure of which is hereby expressly incorporated herein by reference.

FIELD OF THE DISCLOSURE

The present disclosure is directed to a replaceable light source and, more particularly, to a replaceable light source for a field lamp projector and/or an optical distance indicator of a radiation generating device such as a linear accelerator for medical treatment applications.

BACKGROUND

Linear accelerators are typically used to generate radiation for use in medical treatment. To assist with calibration, these devices typically include a field lamp projector and/or an optical distance indicator. Field lamp projectors project a pattern of light through an optical assembly and onto the patient. The pattern of light estimates the pattern of radiation that is to be projected. Optical distance indicators project a light through an optical assembly that includes a lens having a plurality of numbers etched or printed thereon. This results in the projection of one or more numbers on the patient, which indicates to the technician a distance between the radiation generator and the patient. The light sources for these field lamp projectors and optical distance indicators conventionally include halogen bulbs, which create a large sphere of light. To try and focus the light toward the optical assemblies and to reduce reflections in the projectors, apertured plates are often arranged between the bulbs and the optical assemblies.

SUMMARY

One aspect of the present disclosure provides a replacement light apparatus including a base plate a bearing member, and a light source. The bearing member extends from a portion of the base plate. The bearing member includes a bearing surface. The light source is coupled to the bearing surface of the bearing member and adapted to project a cone of light centered on an illumination axis that extends perpendicular to the bearing surface.

Another aspect of the present disclosure provides a replacement light apparatus including a base plate, a grip plate, a bearing member, and a light source. The grip plate extends from a first portion of the base plate. The bearing member extends from a second portion of the base plate. The bearing member includes a bearing surface. The light source is coupled to the bearing surface of the bearing member and adapted to project a cone of light centered on an illumination axis that extends perpendicular to the bearing surface.

Yet another aspect of the present disclosure provides a radiation generating device including a linear particle accelerator, a collimator, and a light projector. The collimator is arranged in proximity to the linear particle accelerator for aligning the particles departing the accelerator and projecting a radiation field. The light projector includes a housing, an optical assembly, and a light fixture. The optical assembly is carried by the housing and has an optical axis. The light fixture is removably disposed in the housing and includes a bearing plate defining a bearing surface. The light source is coupled to the bearing surface and centered on the optical axis. The light source is adapted to project a cone of light centered on an illumination axis that is coaxial with the optical axis.

A still further aspect of the present disclosure includes a method of projecting a pattern of light on a target of a radiation generating device. The method includes emitting a cone of light to produce a pattern of light on the target, wherein the cone of light is emitted along an illumination axis with a light source, the light source being carried by and removably disposed in a projector housing of the radiation generating device.

DETAILED DESCRIPTION

The present disclosure is directed to replaceable light sources for radiation generating devices such as linear accelerators, radiation generating devices including such replaceable light sources, and related methods. The replaceable light sources of the disclosure include light-emitting-diodes (LEDs), as opposed to conventionally used halogen bulbs. As will be described, LEDs provide a more concentrated cone of light in the disclosed examples, which advantageously results in extended life expectancy and increased operational efficiency.

Figure 1:
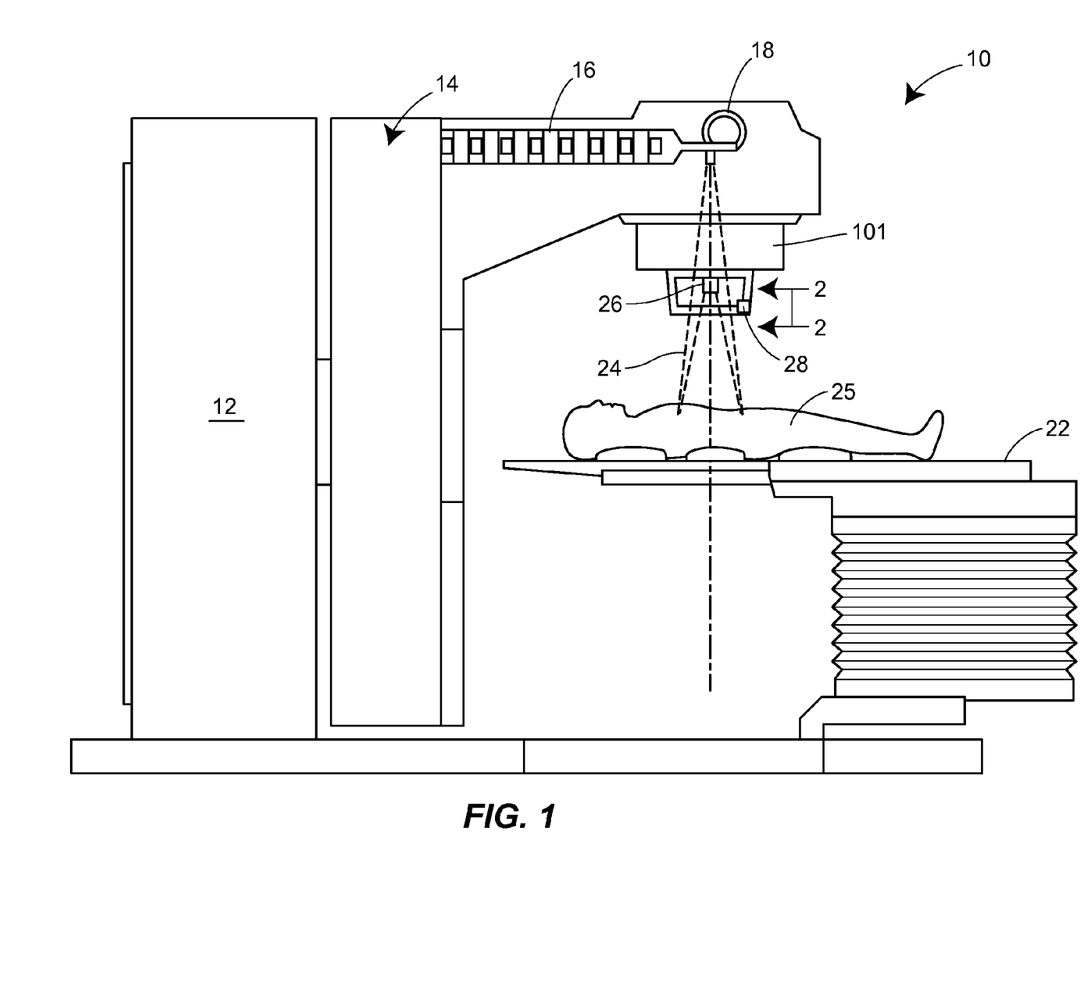
FIG. 1 is a side view of a radiation generating device constructed in accordance with the principles of the present disclosure.

FIG. 1 depicts one version of a radiation generating device 10 constructed in accordance with the principles of the present disclosure. The device 10 includes a stationary support structure 12, a gantry 14, and a bed 22. In the conventional manner, the gantry 14 contains a linear accelerator 16, a bending magnet 18, and a collimator 20 for generating a radiation field 24, as shown, to be projected on a patient 25 lying on the bed 22. In addition to the foregoing, the radiation generating device 10 of FIG. 1 includes a field lamp projector 26 and an optical distance indicator 28 carried within the collimator 20. The field lamp projector 26 is adapted to create a pattern of light on the patient 25 to estimate a pattern of radiation that falls on the patient 24 during operation of the radiation generating device 10. The optical distance indicator 28 projects a light defining one or more numbers on the patient 25, whereby the number(s) indicate a distance between the radiation generator 10 and the patient 25.

Figure 2:
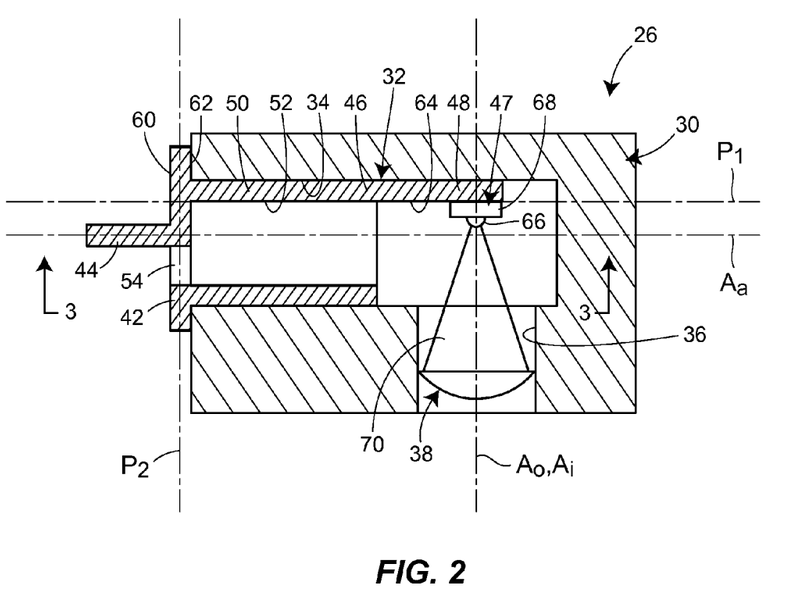
FIG. 2 is a side cross-sectional view of a field lamp projector of the radiation generating device of FIG. 1.

Referring now to FIG. 2, the field lamp projector 26 of the present disclosure includes a projector housing 30 and a light fixture 32. The projector housing 30 defines a socket 34 and an optical cavity 36 that intersects the socket 34. The light fixture 32 is slidably and removably disposed in the socket 34. The optical cavity 36 contains an optical assembly 38. The optical assembly 38 can include one or more lenses 40 disposed along an optical axis Ao for focusing light emitted by the light fixture 32 onto the patient 25. As shown, the light fixture 32 of the presently disclosed version of the disclosure includes a base plate 42, a grip plate 44, a bearing member 46, and a light source 47. In some versions, the base plate 42, grip plate 44, and bearing member 46 can be constructed from a single piece of material such as aluminum, for example, which may be anodized to reduce glare and reflections. In other versions, the base plate 42, grip plate 44, and bearing member 46 can be constructed of different pieces assembled together by welding, brazing, adhesive, or any other suitable means.

Figure 3:
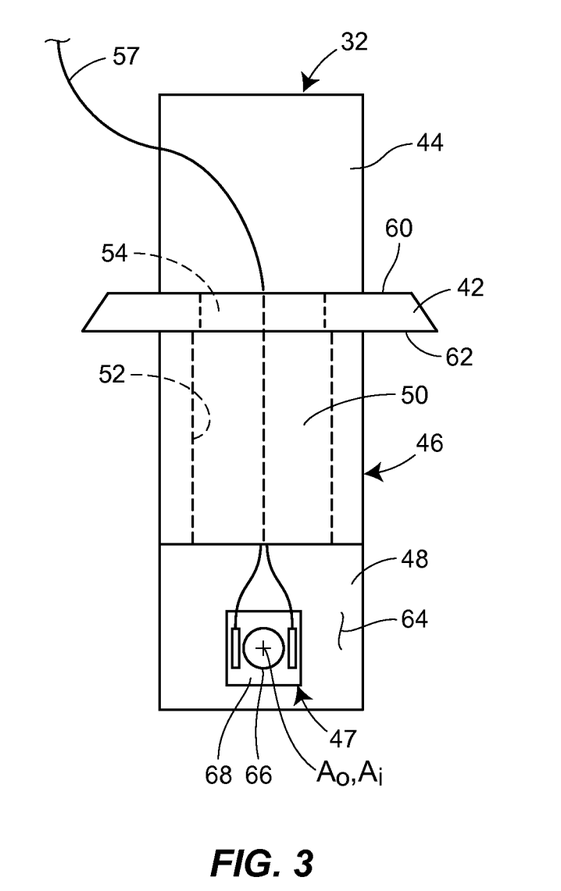
FIG. 3 is a plan view of a light fixture of the field lamp projector of FIG. 2, as if viewed from the perspective of line 3-3 in FIG. 2.

With continued reference to FIG. 2 and additionally to FIG. 3, the base plate 42 of the bearing member 46 can include a generally flat plate having a first surface 60 and a second surface 62 that is opposite the first surface 60. Similar to the base plate 42, the grip plate 44 also can include a generally flat plate and, in the disclosed version, extends perpendicularly from the first surface 60 of the base plate 42. The bearing member 46 extends from the second surface 62 of the base plate 42. In the disclosed version, the bearing member 46 includes a bearing plate 48 and a body portion 50. The bearing plate 48 can be a generally flat plate that defines a bearing surface 64 carrying the light source 47. In the disclosed version, the bearing surface 64 is flat and disposed in a first plane P1 that is perpendicular to a second plane P2, in which the base plate 42 resides. The body portion 50 can be a cylindrical form defining a through bore 52 that at least partially overlaps with an opening 54 in the base plate 42 for accommodating electrical connections 57 (shown in FIGS. 3 and 6) such as one or more wires for connecting the light source 47 to a power source 58 (shown in FIG. 6). The light source 47 of the presently disclosed version includes a light-emitting-diode (LED) 66 mounted on a circuit board 68. In one version, the circuit board 68 can be a 10 mm by 10 mm square circuit board. In another version, the circuit board 68 can be a Southern Linac Universal Mounting Printed Circuit Board, which is a thin, 8 mm thick, FR4 board that utilizes vias and copper pours to enable maximum thermal transfer capabilities. In the depicted version, the light source 47 is mounted flush on the bearing surface 64 of the bearing member 46 and centered on the optical axis Ao of the optical assembly 38. So configured, and as shown, the light source 47 is adapted to project a cone of light 70 that is disposed on an illumination axis Ai, which is coaxial with the optical axis Ao of the optical assembly 38. The illumination axis Ai therefore also extends perpendicular to the first plane P1 and the bearing surface 64 of the bearing member 46. So configured, the light source 47 advantageously directs and concentrates its cone of light 70 in the desired direction along the optical axis Ao, which thereby reduces reflections inside the socket 34 and optical cavity 36 and optimizes the efficiency of the device.

In one version, the light source 47 of the present disclosure can include an LED having a color temperature of 5650 k, exhibiting 235 lumens when running at 700 mA, or 320 lumens when running at 1000 mA. In another version, the light source 47 of the present disclosure can include an LED (e.g., the XP-G2, manufactured by Cree) having a color temperature of 5600 k, exhibiting an output of 254 lumens when running at 700 mA or an output of 458 lumens when running at 1500 mA. LEDs having such characteristics work advantageously well with conventional diffusers used in connection with existing field lamp projectors and optical distance indicators. Additionally, LEDs having such characteristics illuminate well on patient skin. That is, even though such an LED results in a 2 lux reduction relative to conventional halogens, the color temperature of the LED appears brighter to the human eye when projected on skin. One example of an LED that has been tested and found to be suitable includes the Luxeon Rebel LED (Part No. LXML-PWC2) mounted on a 10 mm circuit board. Another example of an LED that has been tested and found to be suitable includes the Cree XP-G2, mounted on the Southern Linac Universal Mounting PCB described above. Yet another example of an LED that can be used is the Luxeon Rebel LED (Part No. LXML-PM01-0100), which emits light having a wavelength of between 520 and 540 nanometers (i.e., green light), and, preferably, a wavelength of approximately 530 nanometers, and which can be mounted on the Southern Linac Universal Mounting PCB described above. This LED has been tested and found to be particularly well-suited for the uses described herein (e.g., illuminating on patient skin). It will of course be appreciated that other LEDs, for example LEDs configured to emit green light having a different wavelength (e.g., a wavelength lower than 520 nm or higher than 540 nm) or LEDs configured to emit light of a different color (e.g., red), can be utilized.

Figure 4:
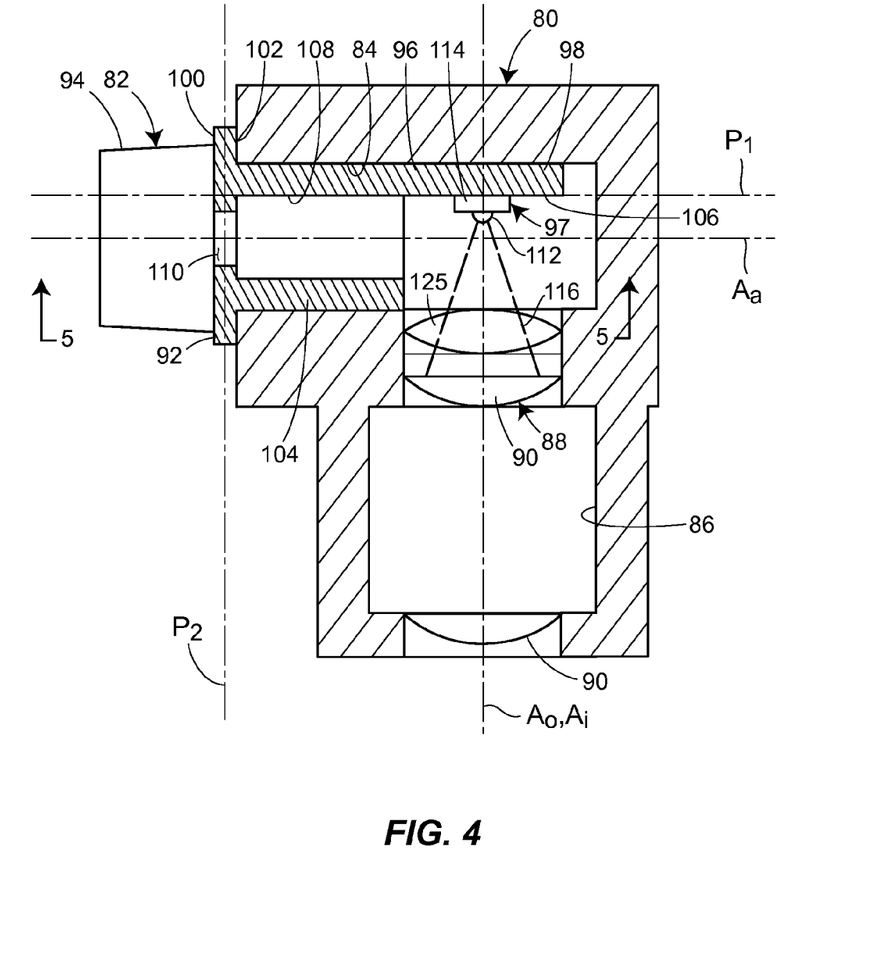
FIG. 4 is a side cross-sectional view of an optical distance indicator of the radiation generating device of FIG. 1.

Referring now to FIG. 4, and as mentioned above, the radiation generating device 10 of the present disclosure can also include the optical distance indicator 28. The optical distance indicator 28 is constructed in a manner very similar to the field lamp projector 26 discussed above, but for the sake of completeness, will also be described herein.

As shown in FIG. 4, the optical distance indicator 28 of the present disclosure includes a projector housing 80 and a light fixture 82. The projector housing 80 defines a socket 84 and an optical cavity 86 that intersects the socket 84. The light fixture 82 is slidably and removably disposed in the socket 84. The optical cavity 86 contains an optical assembly 88. The optical assembly 88 can include one or more lenses 90 disposed along an optical axis Ao for focusing light emitted by the light fixture 82 onto the patient 25. Additionally, in some versions, the optical assembly 88 of the optical distance indicator 28 can include a graduated lens 125 having a plurality of numbers etched, printed or otherwise carried thereon for projecting numbers onto the patient 25, as discussed above. As shown, the light fixture 82 of the presently disclosed version of the disclosure includes a base plate 92, a grip plate 94, a bearing member 96, and a light source 97. In some versions, the base plate 92, grip plate 94, and bearing member 96 can be constructed from a single piece of material such as aluminum, for example, which may be anodized to reduce glare and reflections. In other versions, the base plate 92, grip plate 94, and bearing member 96 can be constructed of different pieces assembled together by welding, brazing, adhesive, or any other suitable means.

Figure 5:
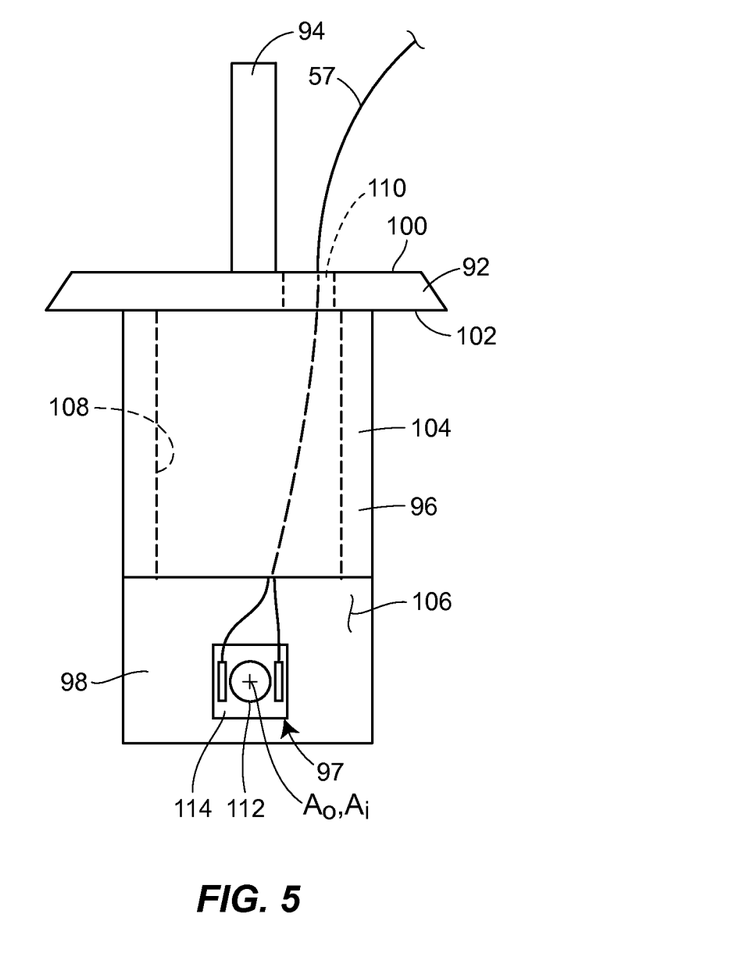
FIG. 5 is a plan view of a light fixture of the optical distance indicator of FIG. 4, as if viewed from the perspective of line 5-5 in FIG. 4.

With continued reference to FIG. 4 and additionally to FIG. 5, the base plate 92 can include a generally flat plate having a first surface 100 and a second surface 102 that is opposite the first surface 100. Similar to the base plate 92, the grip plate 94 also can include a generally flat plate and, in the disclosed version, extends from the first surface 100 of the base plate 92. The bearing member 96 extends perpendicularly from the second surface 102 of the base plate 92. In the disclosed version, the bearing member 96 includes a bearing plate 98 and a body portion 104. The bearing plate 98 can be a generally flat plate that defines a bearing surface 106 carrying the light source 97. In the disclosed version, the bearing surface 106 is flat and disposed in a first plane P1 that is perpendicular to a second plane P2, in which the base plate 92 resides. The body portion 104 can be a cylindrical form defining a through bore 108 that at least partially overlaps with an opening 110 in the base plate 92 for accommodating electrical connections 57 (shown in FIGS. 5 and 6) such as one or more wires for connecting the light source 97 to a power source 58 (shown in FIG. 6). The light source 97 of the presently disclosed version includes a light-emitting-diode (LED) 112 mounted on a circuit board 114. In one version, the circuit board 114 can be a 10 mm by 10 mm square. In another version, the circuit board 114 can be a Southern Linac Universal Mounting PCB, which is a thin, 8 mm thick, FR4 board that utilizes vias and copper pours to enable maximum thermal transfer capabilities. Thus, in some cases, the circuit board 68 and the circuit board 114 can be the same. In the depicted version, the light source 97 is mounted flush on the bearing surface 106 of the bearing member 96 and centered on the optical axis Ao of the optical assembly 98. So configured, and as shown, the light source 97 is adapted to project a cone of light 116 that is disposed on an illumination axis Ai, which is coaxial with the optical axis Ao of the optical assembly 98. The illumination axis Ai therefore also extends perpendicular to the first plane P1 and the bearing surface 106 of the bearing member 96. So configured, the light source 97 advantageously directs and concentrates its cone of light 116 in the desired direction along the optical axis Ao, which thereby reduces reflections and optimizes the efficiency of the device.

Identical to that described above with respect to the field lamp projector 26, the light source 97 of the presently disclosed optical distance indicator 28 can include an LED having a color temperature of 5650 k, exhibiting 235 lumens when running at 700 mA, or 320 lumens when running at 1000 mA. Alternatively, the light source 97 can include an LED (e.g., the XP-G2, manufactured by Cree) having a color temperature of 5600 k, exhibiting an output of 254 lumens when running at 700 mA or an output of 458 lumens when running at 1500 mA. LEDs having such characteristics work advantageously well with conventional diffusers used in connection with existing field lamp projectors and optical distance indicators. Additionally, LEDs having such characteristics illuminate well on patient skin. That is, even though such an LED results in a 2 lux reduction relative to conventional halogens, the color temperature of the LED appears brighter to the human eye when projected on skin. One example of an LED that has been tested and found to be suitable includes the Luxeon Rebel LED (Part No. LXML-PWC2) mounted on a 10 mm circuit board. Another example of an LED is the Luxeon Rebel LED (Part No. LXML-PM01-0100), which emits light having a wavelength of between 520 and 540 nanometers, and, preferably, a wavelength of approximately 530 nanometers, and which can be mounted on the Southern Linac Universal Mounting PCB described above. This LED has been tested and found to be particularly well-suited for the uses described herein (e.g., illuminating on patient skin). It will of course be appreciated that other LEDs, for example LEDs configured to emit green light having a different wavelength (e.g., a wavelength lower than 520 nm or higher than 540 nm) or LEDs configured to emit light of a different color (e.g., red), can be utilized.

Figure 6:
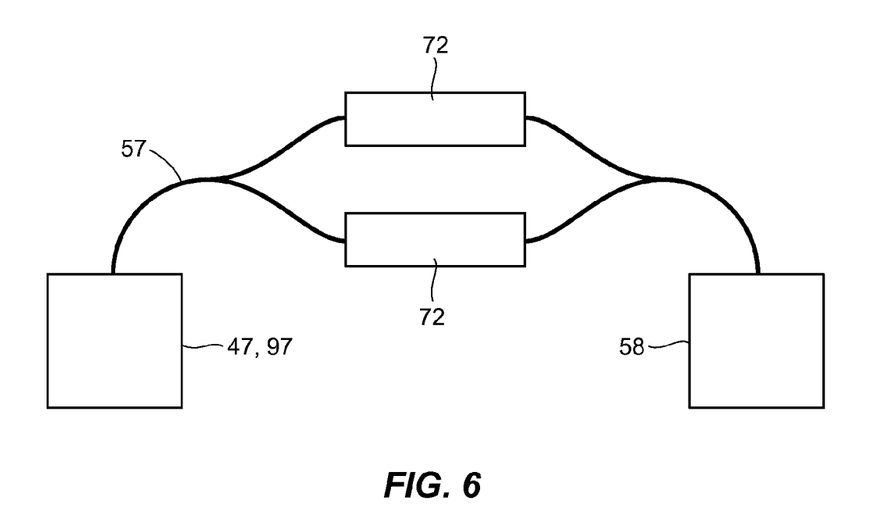
FIG. 6 is a block diagram illustrating an electrical power circuit for both the field lamp projector and optical distance indicator of FIGS. 2-5.
Figure 7:
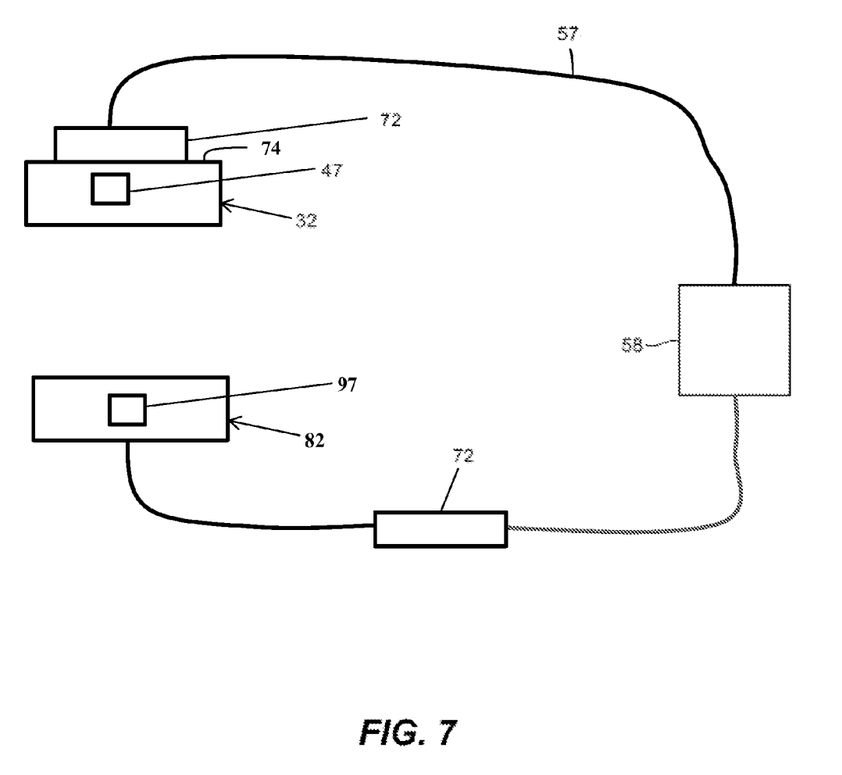
FIG. 7 is a block diagram illustrating an alternative electrical power circuit for both the field lamp projector and optical distance indicator of FIGS. 2-5.

As mentioned above, and with reference to FIG. 6, the light source 47 of the field lamp projector 26 must be connected to a power source 58 in order to generate the desired cone of light 70. As shown in FIG. 6, the light source 97 of the presently disclosed optical distance indicator can be connected to the same power source 58 as the field lamp projector 26 in order to generate the desired cone of light 116. The power source 58 used in conventional devices includes AC power sources, but DC power sources can alternatively be employed. Therefore, because the power source 58 used in conventional devices includes AC power sources, the present disclosure further includes a pair of LED drivers 72 positioned between the power source 58 and the light sources 47, 97. As illustrated in FIG. 6, the LED drivers 72 can be connected in parallel between the power source 58 and the light sources 47, 97. In one version, the parallel drivers 72 can each include a 500 mA AC/DC LED driver such as the LuxDrive 7006 Buckbullet LED driver. Alternatively, as illustrated in FIG. 7, the LED drivers 72 need not be connected in parallel. In the depicted alternative version, one LED driver 72 (e.g., a 1.5 A LED driver such as the Southern Linac LED driver) can be mounted to the light fixture 32 (e.g., to a back 74 of the light fixture 32), and the other LED driver 72 (e.g., a 500 mA AC/DC LED driver such as the LuxDrive 7006 Buckbullet LED driver) can be positioned in the harness that feeds power to the light source 97. In any event, the present disclosure advantageously enables the use of the existing power supply.

From the foregoing disclosure, it can be seen that the LED light sources of the light fixtures 32, 82 disclosed herein advantageously direct and concentrate the generated light along the optical axis Ao of the respective optical assemblies 38, 88. As mentioned, this reduces and/or eliminates reflections within the housing 30, 80. Additionally, because the light sources 47, 97 are directed in this manner, the light fixtures 32, 82 do not include aperture plates disposed between the light sources 47, 97 and optical assemblies 38, 88, as are present in conventional assemblies using halogen bulbs.

From the foregoing disclosure, it can be seen that both the field lamp projector 26 and optical distance indicator 28 are configured to project a pattern of light on a target (i.e., the patient 25). Specifically, this is achieved by energizing the respective LEDs 66, 112 and emitting the respective cones of light 70, 116 to produce a pattern of light on the patient 25. The respective cone of light 70, 116 is emitted along the respective illumination axis Ai with the respective light source 47, 97. Each light source 47, 97 is carried by a projector housing 30, 80 of the radiation generating device 10 and the illumination axis Ai is disposed coaxially with an optical axis Ao of the respective optical assembly 38, 88, which is also carried by the projector housing 30, 80. With the field lamp projector 26 of the present disclosure, emitting the cone of light 70 advantageously produces a pattern of light on the patient which comprises an estimation of a pattern of radiation on the patient 25, which can also be more accurate than estimations provided by conventional halogen light. In contrast, with the optical distance indicator 28, emitting the cone of light 116 includes emitting the cone of light 116 through the optical assembly 88 including the lens 125 carrying the plurality of numbers. So configured, the pattern of light that is projected onto the patient 25 includes one or more numbers indicating a distance between the radiation generating device 10 and the target 25. Once a technician is suitably satisfied with the patterns projected by the field lamp projector 26 and/or optical distance indicator 28, the radiation generating device 10 can be energized to project a radiation field onto the patient 25 in a targeted and specific manner.

Additionally, from the foregoing disclosure, it can be seen that either or both light fixtures 32, 82 of the disclosed projectors 26, 28 can easily be installed into an existing radiation generating device 10 as an upgrade over conventional light fixtures utilizing halogen bulbs. To initiate such an upgrade, a technician can first remove a cover 101 (shown in FIG. 1) from the collimator 20 of the radiation generating device 10, to expose the internal hardware. Then, any existing light fixture can be disconnected from the power source 58. Before or after such disconnection, the existing light fixture can be removed from the light fixture housing 30, 80 by sliding the existing light fixture out along a linear axis Aa (as shown in FIGS. 2 and 4) of the housing socket 64, 84. With the existing light fixture disconnected and out of the way, the upgraded light fixture 32, 82 can be connected to the power source 58 and installed. For installation, the upgraded light source 47, 97 is centered on the optical axis Ao of an optical assembly 38, 88 carried by the respective housing 30, 80. This is achieved by sliding the upgraded light fixture 32, 83 into the respective socket 64, 84 along the linear axis Aa. Once connected, the cover 101 m of the collimator 20 can be re-attached to the radiation generating device 10 and the upgrade process is complete.

The foregoing description is provided as one or more examples embodying the present invention but is not intended to limit the scope of the invention. The scope of the invention is defined by the following claims and includes all equivalents thereof that fall within the spirit and scope of the claims and the disclosure as a whole.

What is claimed:

1. A replacement light apparatus, comprising:
    a base plate;
    a bearing member extending from a portion of the base plate, the bearing member including a bearing plate and a body portion disposed between the base plate and the bearing plate, the bearing plate defining a bearing surface; and
    a light source coupled to the bearing surface of the bearing member and adapted to project a cone of light centered on an illumination axis that extends perpendicular to the bearing surface.

2. The apparatus of claim 1, wherein the bearing surface is disposed in a first plane and the base plate is disposed in a second plane, the second plane being perpendicular to the first plane.

3. The apparatus of claim 1, wherein the light source comprises a printed circuit board mounted on the bearing surface and a light-emitting diode mounted to the printed circuit board.

4. The apparatus of claim 3, wherein the light-emitting diode is configured to emit green light.

5. The apparatus of claim 3, wherein the light-emitting diode is configured to emit light having a wavelength in a range of between 520 nanometers to 540 nanometers.

6. The apparatus of claim 1, wherein the body portion includes a through-bore for accommodating an electrical connection for the light source.

7. The apparatus of claim 1, further comprising a circuit connected to the light source for driving the light source, the circuit including a driver coupled to the bearing member.

8. The apparatus of claim 7, wherein the driver comprises a 1500 mA AC/DC driver.

9. A replacement light apparatus, comprising:
    a base plate;
    a flat, rigid grip element extending from a first portion of the base plate;
    a bearing member extending from a second portion of the base plate, the bearing member including a bearing surface; and
    a light source coupled to the bearing surface of the bearing member and adapted to project a cone of light centered on an illumination axis that extends perpendicular to the bearing surface.

10. The apparatus of claim 9, wherein the light source comprises a light-emitting diode configured to emit green light.

11. The apparatus of claim 9, wherein the light source comprises a light-emitting diode configured to emit light having a wavelength in a range of between 520 nanometers to 540 nanometers.

12. The apparatus of claim 9, wherein the light source comprises a printed circuit board mounted on the bearing surface and a light-emitting diode mounted to the printed circuit board.

13. The apparatus of claim 9, wherein the light source comprises a light-emitting diode, the apparatus further comprising: a power source connected to the light-emitting-diode; and a light-emitting-diode driver connected between the light-emitting-diode and the power source.

14. The apparatus of claim 13, wherein the driver comprises a 1500 mA AC/DC driver.

15. The apparatus of claim 9, wherein the light source is centered on the illumination axis.

16. A radiation generating device, comprising:
    a linear particle accelerator;
    a collimator arranged in proximity to the linear particle accelerator for aligning the particles departing the accelerator and projecting a radiation field; and
    a light projector comprising:
        a housing,
        an optical assembly carried by the housing and having an optical axis, and
        a light fixture removably disposed in the housing, the light fixture including a base plate and a bearing plate extending from a portion of the base plate, the bearing plate comprising a bearing plate and a body portion disposed between the base plate and the bearing plate, the bearing plate defining a bearing surface, and the light fixture further including a light source coupled to the bearing surface and centered on the optical axis, the light source adapted to project a cone of light centered on an illumination axis that is coaxial with the optical axis, wherein the illumination axis extends perpendicular to the bearing surface.

17. The device of claim 16, wherein the light projector comprises a field lamp projector for providing an illuminated estimation of the radiation field projected from the collimator.

18. The device of claim 16, wherein the light projector comprises an optical distance indicator and the optical assembly includes a lens carrying a plurality of numbers for being projected on a radiation target for indicating a distance between the collimator and the target.

19. The device of claim 16, wherein the light source comprises a light-emitting diode configured to emit green light.

20. The device of claim 16, wherein the light source comprises a light-emitting diode configured to emit light having a wavelength in a range of between 520 nanometers to 540 nanometers.

21. The device of claim 16, wherein the light source comprises a printed circuit board mounted on the bearing surface and a light-emitting diode mounted to the printed circuit board.

22. The device of claim 16, wherein the body portion includes a through-bore for accommodating an electrical connection for the light source.

23. The device of claim 16, further comprising a circuit connected to the light source for driving the light source, the circuit including a power source and a driver connected between the power source and the light source, the driver being mounted to a portion of the light fixture.

24. The device of claim 23, wherein the driver comprises a 1500 mA AC/DC driver.

25. The method of claim 23, further comprising projecting a radiation field onto the target with the radiation generating device.

26. A method of projecting a pattern of light on a target of a radiation generating device, the method comprising:
    emitting a cone of light to produce a pattern of light on the target, wherein the cone of light is emitted along an illumination axis with a light source of a light fixture, the light fixture being carried by and removably disposed in a projector housing of the radiation generating device, wherein the light fixture comprises a base plate, a bearing member extending from a portion of the base plate, and a light source, the bearing member including a bearing plate and a body portion disposed between the base plate and the bearing plate, the bearing plate defining a bearing surface, and the light source coupled to the bearing surface of the bearing member, and wherein the illumination axis extends perpendicular to the bearing surface.

27. The method of claim 26, wherein emitting the cone of light comprises emitting, from a light-emitting diode, the cone of light having a wavelength in a range of between 520 nanometers and 540 nanometers.

28. The method of claim 26, wherein emitting the cone of light comprises emitting, from a light-emitting diode, a cone of green light.

29. The method of claim 26, wherein emitting the cone of light to produce a pattern of light comprises estimating a pattern of radiation on the target.

30. The method of claim 26, wherein emitting the cone of light comprises emitting the cone of light through a lens carrying a plurality of numbers such that the pattern of light comprises one or more numbers projected on the target, the one or more numbers indicating a distance between the radiation generating device and the target.

* * * * *

UNITED STATES PATENT AND TRADEMARK OFFICE
CERTIFICATE OF CORRECTION

PATENT NO. : 9,463,075 B2
APPLICATION NO. : 14/269662
DATED : October 11, 2016
INVENTOR(S) : Clark Bowlsbey et al.

It is certified that error appears in the above-identified patent and that said Letters Patent is hereby corrected as shown below:

On the Title Page

At item (57), Line 1, "plate" should be -- plate, --.

In the Claims

At Column 9, Line 19, "The method" should be -- The device --.

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*